United States Patent [19]

Barberet-Maiolino et al.

[11] Patent Number: Plant 7,306

[45] Date of Patent: Aug. 28, 1990

[54] SPRAY CARNATION NAMED LONDISKRA

[75] Inventors: Nicole Barberet-Maiolino; Henri Blanc, both of Antibes, France

[73] Assignee: Laboratoire de Physiologie Vegetale, La Londe-Les-Maures, France

[21] Appl. No.: 266,131

[22] Filed: Oct. 11, 1988

[51] Int. Cl.[5] ..... A01H 5/00

[52] U.S. Cl. ..... Plt./70

[58] Field of Search ..... Plt. 70

*Primary Examiner*—James R. Feyrer

*Attorney, Agent, or Firm*—Charles W. Rummler

[57] ABSTRACT

A new spray carnation variety particularly distinguished by its substantially all white flowers of which the white petals are edged with red both on the top side and on the reverse side presenting a very startling carnation flower, the flowers being of relatively small size and produced profusely on long, strong, spray stems having an average length of about 60 cm. on a plant having vigorous, upright and rigid growth habit, moderately abundant foliage and a total height, at eight months, averaging about 83 cm.

1 Drawing Sheet

BACKGROUND OF THE NEW PLANT

This spray carnation cultivar is believed to be completely new in the spray carnation field and origined as a seedling of a hybrid developed by us through the crossing of two selected carnation varieties from our collection of carnations maintained at our nursery at 83250 La Londe-Les-Maures, France. This particular seedling of the said hybrid, when fully developed, was so unusual that it was immediately selected for propagation and test, which was done by us and under our direction by means of cuttings from the selected plant. The result of this asexual propagation of the selected seedling was so successful that continued propagation of this plant was carried on under our direction at La Londe both by cuttings and by in vitro propagation procedures through several successive generations, which demonstrated conclusively that the distinctive characteristics of the original seedling were fully retained from generation to generation and appeared to be firmly fixed.

DESCRIPTION OF THE DRAWING

This new spray carnation cultivar is illustrated by the accompanying photographic drawing, which shows a substantially complete flowering spray stem showing its general characteristics of flower and form, with the color rendition being as nearly true to that herein specified as can reasonably be expected from conventional, professional photographic procedures.

DESCRIPTION OF THE NEW PLANT

The following is a detailed description of our new spray carnation variety based upon observation of plants grown under glass as well as outdoors at La Londe during the current year, the color designations being according to The R.H.S. Colour Chart published by The Royal Horticultural Society of London, England.

THE PLANT

Origin: Seedling.

Parentage:

*Seed parent.*—Variety 82 MG 7 (unnamed and unpatented).

*Pollen parent.*—Variety 79 MFP 5 (unnamed and unpatented).

Classification:

*Botanic.*—*Dianthus caryophyllus.*

*Commercial.*—Spray Carnation.

Form: Erect bush having at least four stems emitted near the ground.

Height: About 33 cm., in average, at about eight months of growth.

Main stem length: Less than 15 cm. due to pinching.

Branching character: Well branched.

Growth: Vigorous, upright and rigid.

Foliage:

*Quantity.*—Abundant.

*Number of leaves.*—More than 120.

*Leaf size.*—About 10.2 cm. long and about 0.8 cm. wide, at the seventh node.

*Leaf shape.*—Oblong with curved and entire margins.

*Texture.*—Leathery.

*Ribs and veins.*—Hardly noticeable.

*Rachis.*—Hardly noticeable.

*Color.*—Upper side and under side, 189-A.

*Leaflets.*—None.

THE BUD

Size: Small.

*Diameter.*—Averages about 1.2 cm.

*Length.*—Averages about 2.4 cm.

Shape: Ovoid.

Rate of opening: Normal.

Color of petals: When sepals first divide, white edged with red. When petals begin to unfurl, white with red edging.

Sepals:

*Number.*—Five.

*Shape.*—Generally ovate but joined together at the lower part and having an acuminate apex.

*Character.*—The sepals are hooded over the bud but stand up as the flowers open.

*Color.*—Inside, 145-C. Outside, 145-C and 143-C.

*Striae.*—Longitudinal.

Calyx: Long cylindrical.

*Splitting.*—The calyx seldom splits.

*Aspect.*—Smooth.

Flower stem:

*Character.*—Erect and rigid.
*Color.*—189-A.

THE FLOWER

Blooming habit: Recurrent and profusely during the Spring, midseason and Fall growing seasons, with a tendency to give few blooms in the Fall season.
Size of bloom: Small.
*Diameter.*—Averaging about 5.2 cm.
*Depth.*—Averaging about 4.3 cm.
Borne: Singly on an individual stem of the flower cluster.
Shape: When bloom first opens, high centered. When bloom matures, dome-shaped.
Petalage:
*Number of petals.*—Averages about forty-five.
*Arrangement.*—Imbricated.
*Form.*—Fan-shaped with rounded edges and very little serration at the apex.
*Texture.*—Leathery.
*Aspect.*—Satiny.
*Color.*—Outer petals: Body — 155-D. Edge — Between 61-D and 58-B. Base — Greenish. Reverse side — 155-D with edges between Rose Bengal 61-D and China Rose 58-B. Inside petals: The same as the outer petals.
*Petaloids.*—Number. Less than six. Size: Smaller than the petals. Color: The same as the petals.
Flower stem:
*Length.*—Averages about 60 cm. when cut at the tenth node.
*Color.*—189-A.
*Character.*—Upright with good strength.

Fragrance: Perceptible.
Discoloration after full bloom: Very little.
Persistence: The flowers hang on and dry.
Lasting quality: At least ten days as a cut flower in vase keeping.
Disease resistance: Rather tolerant to Fusarium Oxysporum as observed I.N.R.A. 06600 Antibes, France.

REPRODUCTIVE ORGANS

Stamens:
*Number.*—About ten to fourteen.
*Arrangement.*—Encircling the ovary.
Anthers.—Size: About 4 mm. Color: Whitish.
*Filaments.*—Length: Averaging about 1.9 cm. Color: Whitish.
Pistils:
*Number.*—Two or three.
*Styles.*—Length: Averaging about 1.2 cm. Color: Whitish.
*Stigma.*—Color: Whitish.
Character of ovaries: Ribbed.

The plant is an original variety. However, the before mentioned characteristics may be somewhat modulated under various environmental growing conditions as observed in the Spring in the southern part of France.

We claim:

1. The new and distinct spray carnation plant, substantially as herein shown and described, characterized in particular by its substantially all white flower petals, each of which is edged in red, and the recurrent and profuse production of flowers during the Spring, midseason and Fall blooming seasons.

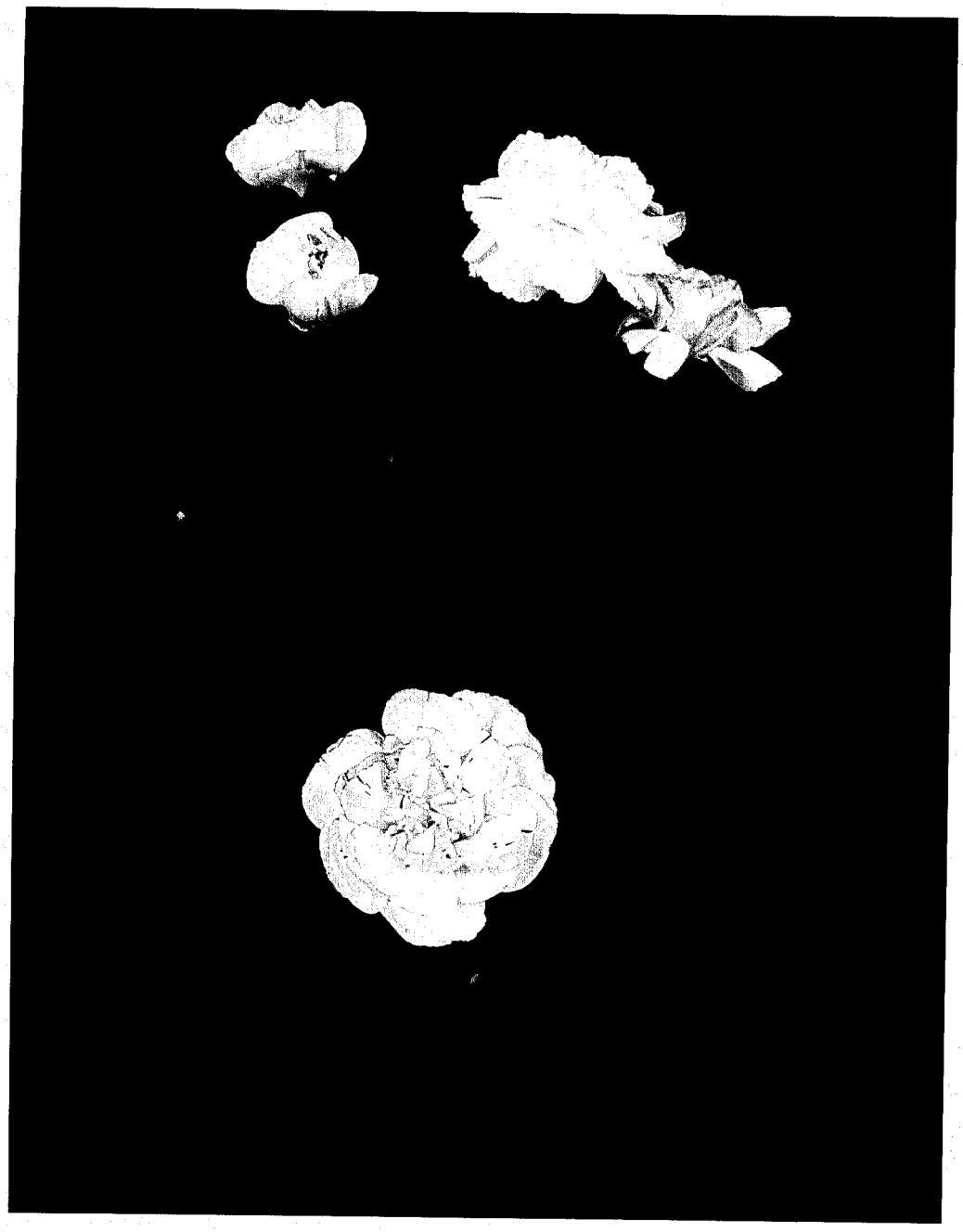

* * * * *